(12) United States Patent
Rothschild et al.

(10) Patent No.: US 6,249,567 B1
(45) Date of Patent: Jun. 19, 2001

(54) X-RAY BACK SCATTER IMAGING SYSTEM FOR UNDERCARRIAGE INSPECTION

(75) Inventors: Peter Rothschild, Chestnut Hill; Lee Grodzins, Lexington, both of MA (US)

(73) Assignee: American Science & Engineering, Inc., Billerica, MA (US)

( * ) Notice: Subject to any disclaimer, the term of this patent is extended or adjusted under 35 U.S.C. 154(b) by 0 days.

(21) Appl. No.: 09/395,331

(22) Filed: Sep. 13, 1999

Related U.S. Application Data

(60) Provisional application No. 60/110,525, filed on Dec. 1, 1998.

(51) Int. Cl.[7] .................................................. G01N 23/201
(52) U.S. Cl. .................................. 378/88; 378/63; 378/86
(58) Field of Search ..................................... 378/86–90, 63

(56) References Cited

U.S. PATENT DOCUMENTS

| | | | |
|---|---|---|---|
| 4,864,142 | 9/1989 | Gomberg | 250/390.04 |
| 5,247,561 | 9/1993 | Kotowski | 378/87 |
| 5,394,454 | * 2/1995 | Harding | 378/88 |
| 5,692,028 | 11/1997 | Geus et al. | 378/57 |
| 5,692,029 | 11/1997 | Husseiny et al. | 378/88 |
| 5,696,806 | 12/1997 | Grodzins et al. | 378/86 |
| 5,764,683 | 6/1998 | Swift et al. | 378/57 |
| 5,910,973 | * 6/1999 | Grodzins | 378/53 |
| 5,974,111 | 10/1999 | Krug et al. | 378/57 |

FOREIGN PATENT DOCUMENTS

| | | | |
|---|---|---|---|
| 0 491 977 A1 | 7/1992 | (EP) | G01V/5/00 |
| 2 277 013 B | 12/1996 | (GB) | . |
| WO 98/03889 | 1/1998 | (WO) | G01V/5/00 |

OTHER PUBLICATIONS

International Search Report Jun. 9, 2000.

* cited by examiner

*Primary Examiner*—Craig E. Church
(74) *Attorney, Agent, or Firm*—Bromberg & Sunstein LLP

(57) ABSTRACT

An inspection system for inspecting a vehicle moving at a grade of travel over a surface and for detecting material disposed within or on the underside of the vehicle. The system has a source for providing a generally upward or downward pointing beam of penetrating radiation of specified cross-section so as to illuminate vehicles driven above or below the source of radiation. A detector arrangement, disposed below the grade of travel, detects radiation from the beam scattered by any material disposed on the underside of the moving vehicle and generates a scattered radiation signal that may be used for characterizing the material disposed on the underside of the vehicle. Similarly, a detector arrangement disposed above the vehicle generates a scattered radiation signal that may be used for characterizing the material disposed within the vehicle.

26 Claims, 2 Drawing Sheets

X-RAY BACK SCATTER IMAGING SYSTEM FOR UNDERCARRIAGE INSPECTION

This application claims priority from U.S. Provisional Application No. 60/110,525, filed Dec. 1, 1998, which is herein incorporated by reference.

TECHNICAL FIELD

The present invention relates to a system and method for detecting materials concealed within, or on, a vehicle, particularly for inspecting the undercarriage of a vehicle when personnel are present within the vehicle.

BACKGROUND OF THE INVENTION

It is desirable to determine the presence of objects, such as contraband, weapons, or explosives, that have been concealed, for example, in a moving vehicle, or, additionally, under the moving vehicle, in either case, without requiring the subjective determination of a trained operator. The determination should be capable of being made while the container is in motion. In case a detection is made, a visual image should be available for verification. The use of images produced by detection and analysis of penetrating radiation scattered from an irradiated object, container, or vehicle is the subject, for example, of U.S. Pat. No. 4,799,247 (Annis et al.) and U.S. Pat. No. 5,764,683 (Swift et al.), where are herein incorporated by reference. The techniques taught in the prior art, however, require that the motion of the inspected object relative to the source of radiation be at a controlled rate, either by moving the inspected object on a conveyor, by sweeping the orientation of the source, or by mounting both source and detector arrangement on a single movable bed and driving them past the inspected object at a known or determinable rate.

The use of x-rays traversing a moving railway car or other large shipping container has been taught in U.S. Pat. No. 5,910,973, issued Jun. 8, 1999, incorporated herein by reference. The '973 patent taught embodiments wherein transmitted x-rays are detected by one or more detectors placed on the side of the car distal to the source of irradiation. Disadvantages of the inspection systems based on transmitted x-rays include their typical insensitivity to organic materials having low attenuation, especially those in sheet form.

SUMMARY OF THE INVENTION

In accordance with one aspect of the invention, in one of its embodiments, there is provided an inspection system for inspecting an underside of a vehicle. The system has a source of radiation for providing an upwardly directed beam of specified cross-section, and a detector arrangement, disposed beneath the surface, for detecting radiation from the beam scattered by any material disposed on the underside of the moving vehicle and for generating a scattered radiation signal. The inspection system also has a controller for characterizing the material disposed on the underside of the vehicle based at least on the scattered radiation signal.

In accordance with alternate embodiments of the invention, the vehicle may be a train car, an automobile, or a truck. The source of penetrating radiation may be an x-ray source and may additionally have a beam scanning mechanism, mechanical or electromagnetic, and the beam direction may be substantially vertically upward. The inspection system may include a display for displaying a scatter image of the material disposed on the underside of the vehicle and may further include a sensor for associating pre-stored characteristics of the vehicle such that the scattered radiation signal may be compared with the pre-stored characteristics.

In accordance with further alternate embodiments of the invention, the source of penetrating radiation of the inspection system may emit x-rays with an end-point energy between 50 and 225 keV, and particularly with an end-point energy of 80 keV, having no appreciable penetration of the underside of the vehicle. The inspection system may have a ramp disposed above the source of penetrating radiation and the detector arrangement such that the vehicle may be driven over the source of radiation and the detector arrangement. The inspection system may have a velocity sensor for registering the velocity of the vehicle with respect to the inspection system and an optical camera for providing an image in visible light of any material disposed on the underside of the moving vehicle. In accordance with yet further embodiments of the invention, the beam of penetrating radiation may have a variable energy spectrum and the controller may characterize the material disposed on the underside of the vehicle based at least on a combination of the scattered radiation signal under conditions of illumination with a first energy spectrum and conditions of illumination with a second energy spectrum.

In accordance with yet further embodiments of the invention, an inspection system is provided for inspecting contents of a vehicle moving at a grade of travel over a surface. The system has a source for providing a beam of penetrating radiation of specified cross-section directed in a beam direction having a dominant vertical component that may be directed upward or downward. The system has a detector arrangement for detecting radiation scattered from the beam by the contents of the moving vehicle and for generating a scattered radiation signal and a velocity sensor for registering the velocity of the vehicle with respect to the inspection system. Finally the system has a controller for characterizing the contents of the vehicle based at least on the scattered radiation signal and the velocity of the vehicle.

BRIEF DESCRIPTION OF THE DRAWINGS

The foregoing features of the invention will be more readily understood by reference to the following detailed description taken with the accompanying drawings.

DETAILED DESCRIPTION OF PREFERRED EMBODIMENTS

Figure 1:
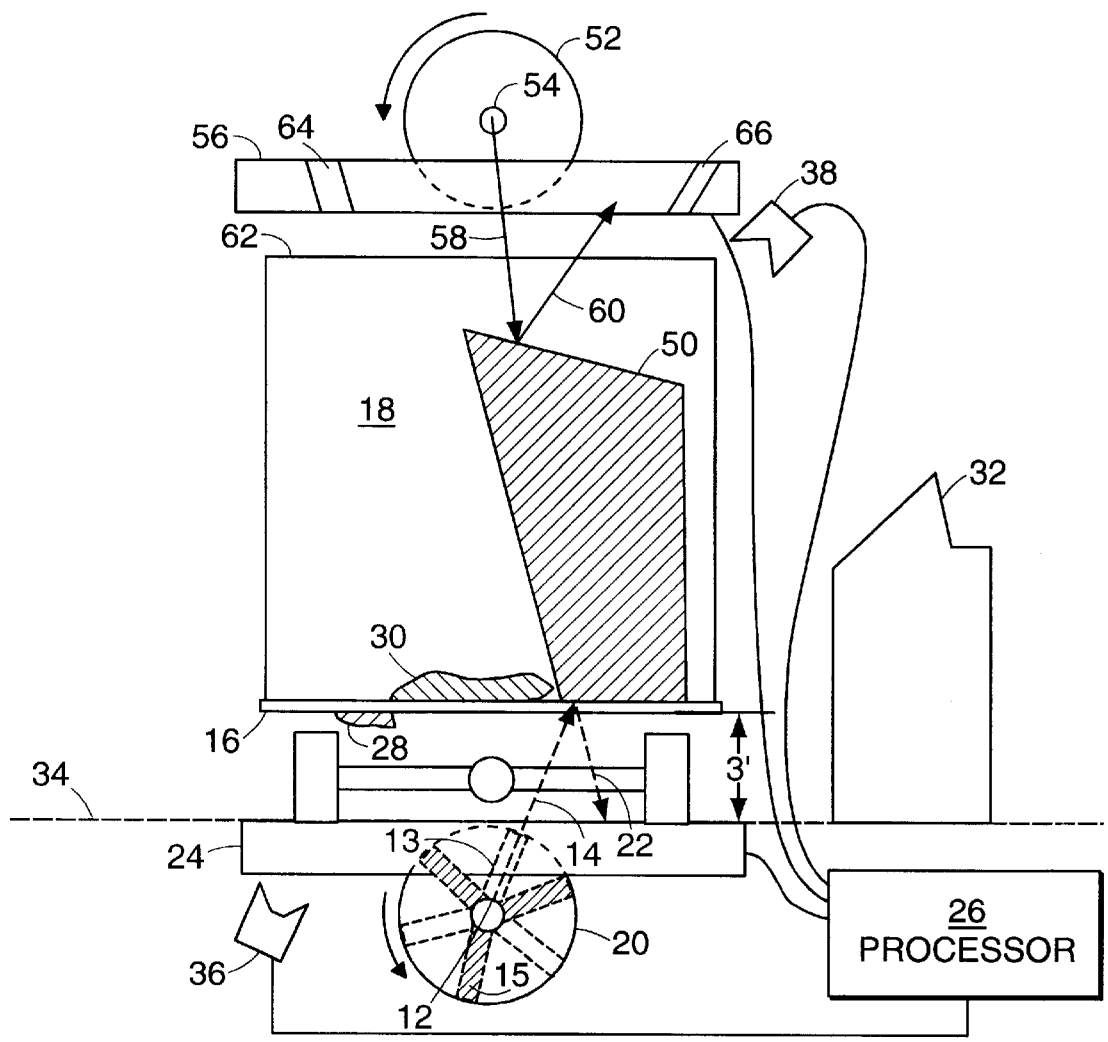
FIG. 1 provides a rear view in cross-section of an inspection system employing a beam for irradiating a piece of rolling stock from below or from above and a detection arrangement for inspection of the rolling stock in accordance with a preferred embodiment of the present invention.

FIG. 1 shows a rear view in cross-section of the elements of an inspection system, designated generally by numeral 10. A source 12 emits penetrating radiation in a beam 14 having a cross-section of a specified shape. Beam 14 of penetrating radiation, may be, for example, a beam of x-rays such as a polychromatic x-ray beam. Source 12 of penetrating radiation is preferably an x-ray tube, for example, however other sources of penetrating radiation such as a LINAC, are within the scope of the present invention. The energy range of the penetrating radiation emitted by source 12 is discussed further below.

A scanning mechanism 20 is provided for scanning beam 14 across one axis of bottom surface 16 of a vehicle 18 or other object that is to be inspected. Scanning mechanism may be a flying spot rotating chopper wheel as known to persons skilled in the art. Alternatively, electromagnetic scanners may be employed. In accordance with one embodiment, an electromagnetic scanner includes a charge particle beam that may be accelerated towards, and electromagnetically scanned across, a target, thereby generating x-rays that emanate from a succession of points on the target. The emitted x-rays may pass through one or more collimator apertures, thereby creating a sequence of beams have distinct orientations. Various embodiments of an electromagnetic scanner are described in co-pending U.S. Provisional Application 60/140,767, filed Jun. 24, 1999 and entitled "Method And Apparatus For Generating Sequential Beams of Penetrating Radiation," which is incorporated herein by reference.

Inspected object or container 18 may be self-propelled through beam 14 or may be pulled by a mechanized tractor, or by a conveyor of any sort. Container 18 is typically a train car, and is depicted as such in FIG. 1, where cargo car 18 of a train is shown being pulled along a track in a direction into the page. It is to be recognized that, equivalently, beam 14 may move with respect to object 18 in a direction into the page.

Beam 14 will be referred to in the present description, without limitation, as an x-ray beam. In accordance with a preferred embodiment of the invention, rotating chopper wheel 20 is used to develop a pencil beam 14 which may be swept in a plane substantially parallel to that of the page. The formation of pencil beam 14 by a series of tubular collimators 13 distributed as spokes on rotating wheel 20 is known in the art. The cross section of pencil beam 14 is of comparable extent in each dimension and is typically substantially rectangular, although it may be many shapes. The dimensions of pencil beam 14 typically define the scatter image resolution which may be obtained with the system. Other shapes of beam cross section may be advantageously employed in particular applications, and all shapes, including, in particular, fan beams, are within the scope of the present invention as described herein and in any appended claims. Fan beams may be employed, particularly, in an application of imageless contraband detection.

Figure 2:
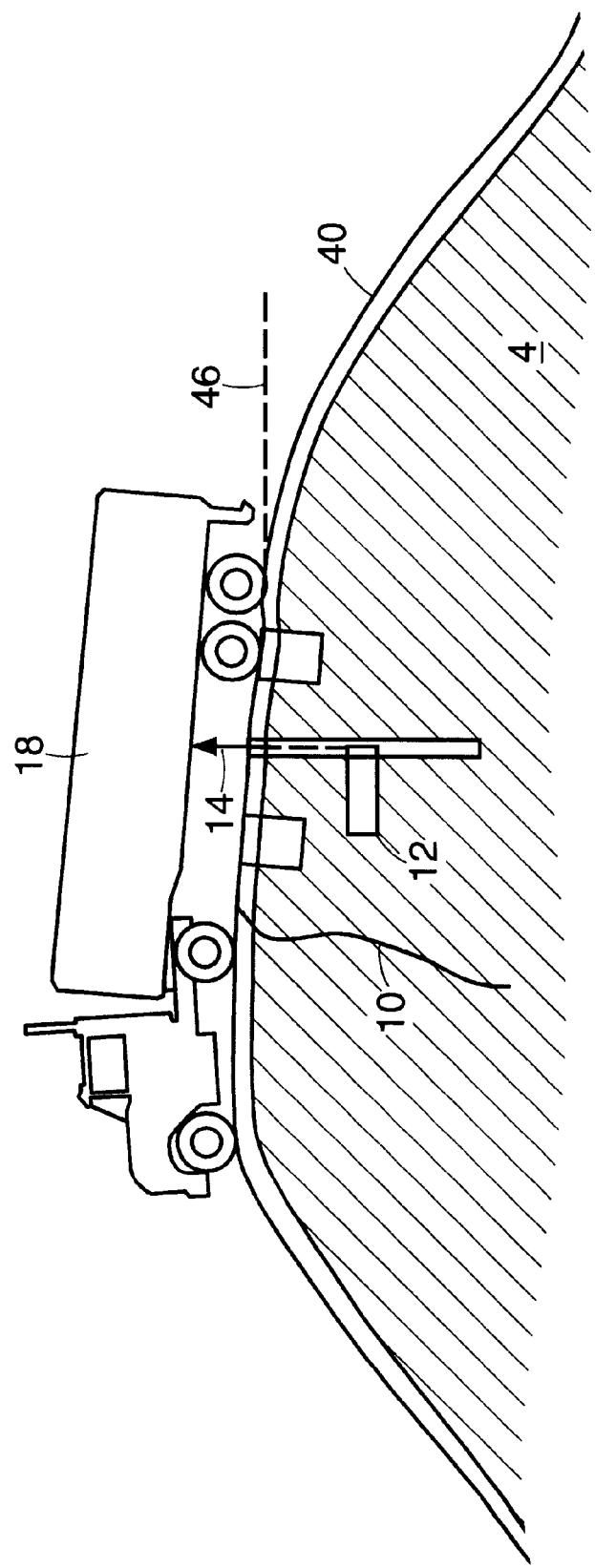
FIG. 2 is a side view in cross-section of an undercarriage inspection system deployed beneath a ramp in accordance with an embodiment of the present invention.

A detector arrangement is disposed beneath the plane or grade of locomotion of vehicle 18. X-rays 22 scattered by Compton scattering out of beam 14 in an essentially backward direction are detected by one or more backscatter detectors 24 placed either at or below grade level 34. Grade level, as used herein, refers to the plane 46 above which container 18 is traveling at the time of inspection. Grade level may thus refer to the ground level, in the case of inspection systems permanently installed below ground level, or to the upper level of a ramp, where the inspection system, disposed beneath the ramp, may advantageously be moved from one site to another. Grade level, when referring to inspection of rolling stock refers to the top of the track. FIG. 2 shows an embodiment of the invention in which a track 40 or other form of ramp is provided to allow vehicle 18 to be driven above inspection system 10. Container 18 may be pulled or self-propelled in traversing the inspection site. As discussed above, an x-ray source 12 and a scanning mechanism 20 provide a beam 14 of penetrating radiation that has a vertically-directed component as it traverses plane 46 above which container 18 is disposed as the inspection is conducted. Inspection system 10 may be configured within a ground cavity 42 (shown in FIG. 1) or, otherwise, above the ground 43 and beneath ramp 40, as shown in FIG. 2.

Within the scope of the invention, any x-ray detection technology known in the art may be employed for backscatter detector arrangement 24. The detectors may be scintillation materials, either solid or liquid or gaseous, viewed by photo-sensitive detectors such as photomultipliers or solid state detectors. Liquid scintillators which may be doped with tin or other metal. Respective output signals from the scatter detectors 24 are transmitted to a processor 26, and processed to obtain images of object 28 on the underside of bottom surface 16 of vehicle 18 or of object 30 on the floor inside the vehicle.

Other characteristics may be obtained using backscatter techniques, such, for example, as mass, mass density, mass distribution, mean atomic number, or likelihood of containing targeted threat material, all as known to persons skilled in the art of x-ray inspection.

In accordance with preferred embodiments of the invention, two modes of operation may be employed. In accordance with a first mode of operation, x-rays are employed having a distribution of energies with a maximum energy (end-point energy) low enough such that no significant amount of radiation penetrates the undercarriage. For cars with relatively thin sheet metal flooring, the end-point energy may be restricted to 50 keV or 80 keV. For trains with heavy steel flooring, the end point energy may be as high as 150 keV. Only materials concealed in the undercarriage are detected, and there is no radiation dose to the driver. In this mode of operation, the driver may be within the vehicle during inspection of the underside of the vehicle.

A second operating mode uses x-ray energies up to about 160 keV. At this energy, there is more penetration into the vehicle, and large organic objects that have been placed on the floor inside the vehicle can be detected. End-point energies of between 50 and 225 keV may advantageously provide undercarriage inspection without excessive penetration of upper regions of the inspected vehicle.

Under certain circumstances, inspection of vehicle 18 by means of penetrating radiation directing from above the vehicle may be advantageous. In cases where inspection from above is performed, an x-ray source 54 is provided above the vehicle and a scanning mechanism 52 such as the mechanical chopper wheel 52 shown in FIG. 1. As wheel 52 is rotated, x-ray beam 58 emerges from hollow spokes of wheel 52 in the same manner as described with respect to wheel 20. The illuminating x-ray beam 58 sweeps across top 62 of container 18. X-rays 60 scattered by objects 50 within vehicle 18 are detected by scatter detectors 56 disposed either side of scanning mechanism 52.

The top of a cargo van is typically thinner and more easily penetrated by radiation than either the sides or bottom of the van. Thus the ceiling may provide the least interference to a backscatter view of the interior. Protection of personnel may be provided by the thicker gauge steel of the roof of the cab, or, alternatively, scanning may be initiated only during passage of the trailer.

Various methods known in the art may be employed for determining the location in three dimensions of the contents 50 of container 18. For example, the use of detector elements 64 and 66 asymmetrically disposed with respect to source 54 may be used to determine the depth of scattering material in accordance with an algorithm described in co-pending U.S. Provisional patent application, Ser. No. 60/112,102, filed Dec. 14, 1998, which is herein incorporated by reference.

As vehicle 18 passes the inspection point, an inspection is performed, resulting either in the triggering of an alarm, under specified conditions, or a two-dimensional scatter image may be displayed to an operator, at console 32. Additionally, an alarm may be triggered and an image displayed. The motion of vehicle 18 may be monitored by known sensor means to provide a scaling of the axis of the image along the direction of motion. In particular, a measure of the instantaneous speed may be obtained by means of any sort of velocity sensor 38 such as a microwave Doppler sensor, for example. Knowledge of the instantaneous speed of the vehicle allows undistorted images of the undercarriage of the vehicle to be obtained by adjusting pixel width and position (registration) according to vehicle speed, as known to persons skilled in imaging.

In accordance with alternate embodiments of the invention, automatic algorithms may be used to detect regions of enhanced backscatter in the image or regions meeting other specified criteria with respect to size, shape or composition. When such a region is detected, the operator is alerted, and the suspicious area is high-lighted for the operator on the backscatter image. For checkpoints into controlled facilities, in accordance with a further embodiment, a sensor, such as a bar-code reader, enables the backscatter image to be compared by a processor with a pre-stored features of the vehicle undergoing inspection which may correspond to a spatial regularity of highly scattering members, for example.

In accordance with a further embodiment of the invention, a dual-energy technique is employed for obtaining two views (or a combined view) of the vehicle undercarriage in order to detect organic contraband automatically. A dual-energy backscatter technique is especially useful when the end point energy of the x-ray beam may exceed about 80 keV. Referring again to FIG. 1, a 160 kV x-ray source 12 with a tungsten anode may be employed, for example, with a beam-forming chopper wheel with six spokes 13. An energy-selective x-ray absorber 15 is placed in alternate arms so as to absorb out the lower-energy components of the x-ray spectrum thereby producing an x-ray beam having a spectrum in which most of the intensity of the beam is at energies greater than about 80 keV. The backscatter view taken with the absorber-filled spokes is thus produced by the high-energy radiation in the x-ray beam.

A view taken with the energetic beam (through an absorber-filled spoke) may be combined, in accordance with embodiments of the invention, with a view taken with a beam containing a more substantial fraction of low-energy photons. Combination may be performed using one or more of a variety of algorithms known in the art for combining scatter images. For example, the ratio of the intensities of corresponding pixels may be taken, thereby providing a higher level of confidence in a determination of atomic number than may be obtained in either view taken alone. The high-energy view is dominated by Compton scattering, which is substantially independent of the scattering material. The low-energy view may be dominated by the photoelectric effect, which is strongly material-dependent. The ratio of the two views thus provides a measure of the material qualities substantially independent of geometrical effects and changes in signal output having their origin in temperature of component variability. Thus, source-object and detector-object variations may be normalized out, using algorithms known in the art. Additionally, data or images obtained from detected scattered radiation may be combined with optical images, obtained with a video camera 36 (shown in FIG. 1), for example, so that images of suspected contraband, obtained with modest spatial resolution, may be superposed on a high-resolution optical image for evaluation by an operator.

The described embodiments of the invention are intended to be merely exemplary and numerous variations and modifications will be apparent to those skilled in the art. All such variations and modifications are intended to be within the scope of the present invention as defined in the appended claims.

We claim:

1. An inspection system for inspecting an underside of a vehicle moving at a grade of travel over a surface, the system comprising:
   a. a source for providing a beam of penetrating radiation of specified cross-section directed in a beam direction having a dominant vertical component wherein the source of penetrating radiation emits x-rays with no appreciable penetration of the underside of the vehicle;
   b. a detector arrangement for detecting radiation from the beam scattered by any material disposed on the underside of the moving vehicle and for generating a scattered radiation signal; and
   c. a controller for characterizing the material disposed on the underside of the vehicle based at least on the scattered radiation signal.

2. The inspection system as set forth in claim 1, wherein the vehicle is chosen from the group of a train car, an automobile, and a truck.

3. The inspection system as set forth in claim 1, wherein the detector arrangement is disposed beneath the grade of travel.

4. The inspection system as set forth in claim 1, wherein the source of penetrating radiation is an x-ray source.

5. The inspection system as set forth in claim 1, wherein the source of penetrating radiation includes a beam scanning mechanism.

6. The inspection system as set forth in claim 1, wherein the beam direction is substantially vertically upward.

7. The inspection system as set forth in claim 6, wherein the beam scanning mechanism is a rotating chopper wheel.

8. The inspection system as set forth in claim 6, wherein the beam, scanning mechanism is an electromagnetic scanner.

9. The inspection system as set forth in claim 1, wherein the beam of penetrating radiation is a pencil beam.

10. The inspection system as set forth in claim 1, further including a display for displaying a scatter image of the material disposed on the underside of the vehicle.

11. The inspection system as set forth in claim 1, further including a sensor for associating pre-stored characteristics of the vehicle such that the scattered radiation signal may be compared with the pre-stored characteristics.

12. The inspection system as set forth in claim 1, wherein the source of penetrating radiation emits x-rays with an end-point energy between 50 and 225 keV.

13. The inspection system as set forth in claim 1, wherein the source of penetrating radiation emits x-rays with an end-point energy below 80 keV.

14. The inspection system as set forth in claim 1, further comprising a ramp disposed above the source of penetrating radiation and the detector arrangement such that the vehicle may be driven over the source of radiation and the detector arrangement.

15. The inspection system as set forth in claim 1, further comprising a velocity sensor for registering the velocity of the vehicle with respect to the inspection system.

16. The inspection system as set forth in claim 1, wherein the beam of penetrating radiation has a variable energy spectrum.

17. The inspection system as set forth in claim 1, wherein the detector arrangement includes at least two detectors disposed asymmetrically with respect to the source.

18. The inspection system as set forth in claim 1, further comprising an optical camera for providing an image in visible light of any material disposed on the underside of the moving vehicle.

19. The inspection system as set forth in claim 18, wherein the controller characterizes the material disposed on the underside of the vehicle based at least on combination of the scattered radiation signal under conditions of illumination with a first energy spectrum and the scattered radiation signal under conditions of illumination with a second energy spectrum.

20. The inspection system as set forth in claim 18, further comprising a display for presenting the image provided by the optical camera in registration with an image generated from the scattered radiation signal.

21. The inspection system as set forth in claim 20, wherein the display is a single video monitor.

22. A method for inspecting an underside of a vehicle moving over a surface, the method comprising:
   a. illuminating the underside of the vehicle with penetrating radiation formed into a beam such that the penetrating radiation does not appreciably penetrate the underside of the vehicle;
   b. detecting radiation from the beam scattered by any material disposed on the underside of the moving vehicle to generate a scattered radiation signal; and
   c. characterizing the material disposed on the underside of the vehicle based at least on the scattered radiation signal.

23. A method according to claim 22, further including:
   d. displaying a scatter image of the scattered radiation signal.

24. A method according to claim 22, further including:
   d. varying the orientation of the beam with respect to the vehicle.

25. A method according to claim 22, wherein the step of illuminating the underside of the vehicle includes illuminating with penetrating radiation having a first spectral composition and then illuminating with penetrating radiation having a second spectral composition.

26. A method according to claim 25, wherein the step of characterizing the material disposed on the underside of the vehicle includes combining the scatter radiation signal obtained during illumination with the first spectral composition with the scatter radiation signal obtained during illumination with the second spectral composition.

* * * * *